United States Patent [19]

Onopchenko et al.

[11] 3,978,119

[45] Aug. 31, 1976

[54] PROCESS FOR CONVERTING STILBENE OR BIBENZYL TO NITROBENZOIC ACIDS

[75] Inventors: Anatoli Onopchenko, Monroeville; Johann G. D. Schulz, Pittsburgh, both of Pa.

[73] Assignee: Gulf Research & Development Company, Pittsburgh, Pa.

[22] Filed: July 11, 1975

[21] Appl. No.: 595,157

[52] U.S. Cl............................................ 260/523 R
[51] Int. Cl.².................................... C07C 51/33
[58] Field of Search..................... 260/523 R, 524 N

[56] References Cited

UNITED STATES PATENTS 2,695,311  11/1954  Emerson et al................. 260/524 N

*Primary Examiner*—James O. Thomas, Jr.
*Assistant Examiner*—A. Siegel

[57] ABSTRACT

A process for converting stilbene or bibenzyl to nitrobenzoic acids, particularly para-nitrobenzoic acid, which involves nitrating stilbene or bibenzyl and then oxidizing the nitrated product.

7 Claims, No Drawings

PROCESS FOR CONVERTING STILBENE OR BIBENZYL TO NITROBENZOIC ACIDS

BACKGROUND OF THE INVENTION

1. Field of the Invention

This invention relates to a process for converting stilbene or bibenzyl, or combinations thereof, to nitrobenzoic acid, particularly para-nitrobenzoic acid, by subjecting the stilbene or bibenzyl to nitration and then subjecting the nitrated aromatic compound to oxidation.

2. Description of the Prior Art.

Aromatic compounds can be nitrated. Aromatic compounds carrying oxidizable substituents on the ring can be subjected to oxidation conditions to obtain the corresponding carboxylic acid. We are unaware that the art discloses or teaches that stilbene or bibenzyl can be subjected to nitration and then to oxidation in the manner defined herein to obtain a product containing a large amount of nitrobenzoic acids, the predominant nitrobenzoic acid being para-nitrobenzoic acid.

SUMMARY OF THE INVENTION

We have found that stilbene or bibenzyl, or combinations thereof, can be converted in high yield to a product predominating in nitrobenzoic acid, particularly para-nitrobenzoic acid, by a process which comprises nitrating the defined aromatic compound with concentrated nitric acid and then subjecting the nitrated aromatic compound to oxidation with dilute nitric acid. Insofar as the aromatic charge employed herein, by "stilbene" we means to include trans-stilbene.

The aromatic charge herein is subjected to nitration in a manner such that no more than one nitro group is placed on an individual aromatic ring. This can be done following conventional nitration procedures. For example, to an aqueous nitric acid solution having a concentration of about 40 to about 95 weight per cent, preferably about 70 to about 90 weight per cent, there is added, while stirring, the defined aromatic charge. The amount of nitric acid needed is that amount sufficient to place one nitro group on each of the rings of the aromatic charge and to maintain the resultant nitrated product obtained in solution. In general, about three to about 10, preferably about 3 to about 5 parts by weight of nitric acid, as 100 per cent nitric acid, is sufficient to effect such purposes. The temperature during nitration can vary over a wide range, for example, from about −20° to about 100°C., preferably from about −10° to about 60°C. Pressure does not affect the course of the reaction and pressures up to about 100 pounds per square inch gauge (about seven kilograms per square centimeter), or even higher, can be used, but in general atmospheric pressure is sufficient. The time required for nitration can also vary over a wide range, for example, from about 15 minutes to about 12 hours, but, in general, a period of about ½ hour to about 2 hours is sufficient. In order to facilitate the nitration reaction, conventional dehydrating agents, such as sulfuric acid or acetic anhydride, can be present, for example, in an amount that can be in the range of about 10 to about 300, preferably about 20 to about 100, weight per cent, based on the weight of the nitric acid.

The nitrated aromatic compound obtained above is then subjected to conventional nitric acid oxidation to obtain the desired product predominating in para-nitrobenzoic acid. If the nitration procedure defined above has been carried out in the presence of a dehydrating agent, as described, the dehydrating agent is first removed from the nitrated product before oxidation, since the presence of the dehydrating agent during oxidation can interfere with the smooth operation of the oxidation reaction. Thus, at the relatively high temperatures used during oxidation, the nitric acid will tend to oxidize the acetic anhydride, thus consuming valuable nitric acid and forming undesirable compounds, and the sulfuric acid will tend to sulfonate the nitrated product and can react with the metal walls of the reactor. Removal of the dehydrating agent can be effected in any conventional manner. For example, this can be done by diluting the nitrated reaction product at room temperature with a large amount of water at room temperature and then recovering the precipitated nitrated product by filtration. The recovered nitrated aromatic product can then be subjected to oxidation with fresh nitric acid as described hereinafter. If no dehydrating agent has been used, the nitrated aromatic product can also be similarly recovered and subjected to oxidation, as described hereinafter, or, preferably, the total nitrated aromatic product is diluted with sufficient water to obtain a nitric acid concentration sufficient for oxidation and then the resultant mixture is subjected to oxidation, as described hereinafter.

The nitric acid oxidation of the nitrated aromatic product obtained above can be effected, for example, by oxidizing the same, while stirring, with aqueous nitric acid having a concentration of about five to about 50 weight per cent, preferably about 10 to about 40 weight per cent. The amount of nitric acid, as 100 per cent nitric acid, used can vary over a wide range, but, in general, at least about 1 part of nitric acid, preferably about 2.5 to about 5.0 parts by weight of nitric acid, per part by weight of nitrated aromatic product is sufficient. The temperature during reaction can be in the range of about 160° to about 220°C., preferably about 170° to about 190°C. Pressure seems to have no appreciable effect on the course of the reaction. In general a pressure of about 200 to about 500 pounds per square inch gauge (about 14 to about 35 kilograms per square centimeter), preferably about 250 to about 400 pounds per square inch gauge (about 17.6 to about 28.2 kilograms per square centimeter) is sufficient. A reaction time of about ½ to about 12 hours, preferably about one to about four hours, will suffice. As a result of such oxidation, a reaction product predominating in para-nitrobenzoic acid is obtained containing lesser amounts of ortho- and meta-nitrobenzoic acids.

The recovery of the nitrobenzoic acids from the oxidation can be effected in any convenient or conventional manner. For example, the reaction mixture is cooled to room temperature and then depressured and subjected to filtration to recover a first, or major, crop of nitrobenzoic acids. To recover the remainder of the nitrobenzoic acids the filtrate can be evaporated to dryness, dissolved in sodium hydroxide solution and filtered to remove a sodium hydroxide insoluble sludge. The filtrate, which is essentially the sodium salts of nitrobenzoic acids, is acidified with HCl and evaporated to dryness to produce sodium chloride and nitrobenzoic acids. Separation of the two from each other can be effected by extraction with a solvent, such as acetone to obtain a solution containing the nitrobenzoic acid. The sodium chloride is discarded and the solution is evaporated to dryness to obtain the second crop of nitrobenzoic acids. If desired, the nitrobenzoic acid mixture obtained can be treated in any conventional manner to separate and recover the individual isomers therein, for example, as in British Pat. No. 1,068,535. For some applications the total mixture of nitrobenzoic acids can be used as such, without separation into its individual isomers, for example, as plant growth inhibitors, antiviral agents, etc. If desired, the nitrobenzoic acids herein can be converted to the corresponding aminobenzoic acids in any conventional manner, for example, by following the procedure disclosed in U.S. Pat. Nos. 2,947,781 and 3,324,175.

DESCRIPTION OF PREFERRED EMBODIMENTS

A number of runs were carried out wherein trans-stilbene or bibenzyl were added slowly, with stirring, to concentrated nitric acid to obtain a nitrated aromatic product. The product so obtained, except for the one of the runs using bibenzyl charge, identified as Run No. II in Table I below, was then diluted with water to obtain a desired nitric acid concentration therein. In Run No. II the nitrated aromatic product was poured into a large amount of water and the precipitate formed (which was the desired nitrated bibenzyl) was recovered by filtration. The latter was then mixed with dilute nitric acid. Each of the mixtures so prepared was then subjected to oxidation with the dilute nitric acid. The oxidation product obtained was cooled to room temperature and then depressured. Filtration of the product resulted in the recovery of a first crop of nitrobenzoic acids and treatment of the filtrate in the manner defined above resulted in the recovery of a second crop of nitrobenzoic acids.

The results obtained herein are tabulated below in Table I. Included also in Table I, for reasons that will be apparent below are data obtained by L. Fortina and R. Passerini in *Boll, Sci. fac. chim. ind. Bologna*, 17,1–4 (1959), reported in *Chemical Abstracts*, 53, 17928a (1959), wherein they oxidized trans-stilbene.

nitrobenzoic acid 13 and 17.4 weight per cent, respectively, and ortho-nitrobenzoic acid 1 and 4.9 weight per cent, respectively. For purposes of calculating yields in the above Table, it is assumed that each aromatic unit in the charge is capable of producing one unit of a benzoic acid. The yield then would be the actual mols of nitrobenzoic acid obtained over the theoretical yield times 100.

The results obtained above are most unusual. As noted above, the results obtained by Fortina et al when they subjected trans-stilbene to nitric acid oxidation are also included in Table I for comparison. Note that using conventional nitric acid oxidation, as in the present case, Fortina et al obtain a yield of benzoic acid of 17 per cent. Accordingly, it might be argued that had these compounds been nitrated prior to oxidation, a nitrobenzoic acid might be obtained instead of the benzoic acid obtained by Fortina et al, the yield of nitrobenzoic acid, nevertheless, would be on the same order of magnitude. Note, however, that in the process defined and claimed herein a yield of nitrobenzoic acid of from 75 to 79 per cent is obtained, which is at least 4 times more than expected. That similar good results are also obtained with bibenzyl is similarly surprising.

The process defined herein not only results in the production of a large amount of nitrobenzoic acids from the defined aromatic compounds, but also results in the production of predominant amounts of the desired para isomer thereof. If one were to take the benzoic acid produced by Fortina et al and were to nitrate the same, not only would he obtain a correspondingly small amount of nitrobenzoic acid, as shown far lower than would be obtained herein, but the isomer produced would be the less desirable meta isomer, since it is well known that a carboxyl group on an aromatic ring is a meta directing group toward electrophilic substitution.

The nitrobenzoic acids prodced herein are old and well known and have many utilities. Thus, they can be

TABLE I

| Charge | I | II | III | Fortina Et Al Run |
|---|---|---|---|---|
| Substrate | Trans-Stilbene | Bibenzyl | Bibenzyl | Trans-Stilbene |
| Weight In Grams | 30 | 50 | 35 | 22.2 |
| Reaction Conditions | | | | |
| Nitration | | | | |
| HNO$_3$ Concentration | 90 | 90 | 70 | — |
| Weight of HNO$_3$ (As 100 Per Cent HNO$_3$), Grams | 187 | 300 | 74 | — |
| Temperature, °C. | −10 | −15 | 65 | — |
| Pressure, Pounds Per Square Inch Gauge | ←——— Atmospheric ———→ | | | — |
| Reaction Time, Hours | 1.0 | 1.5 | 6.5 | — |
| Oxidation | | | | |
| HNO$_3$ Concentration | 40 | 38 | 35 | 30 |
| Weight of HNO$_3$ (As 100 Per Cent HNO$_3$), Grams | 168 | 270 | 153 | 36 |
| Temperature, °C. | 180 | 182 | 185 | 212 |
| Pressure, Pounds Per Square Inch Gauge | 370 | 240 | 235 | 510 |
| (Kilograms Per Square Centimeter) | (26) | (16.8) | (16.5) | (36) |
| Reaction Time, Hours | 1.0 | 1.0 | 1.0 | 1.25 |
| Yield Data | | | | |
| Product Obtained | ←——— Nitrobenzoic Acids ———→ | | | ←— Benzoic Acid —→ |
| Weight of Product, Grams | 41.5 | 39.0 | 50.7 | 5.3 |
| Yield, Per Cent | 75 | 71 | 79 | 17 |

In the above Table the product in Run No. I was found to contain 79 weight per cent para-nitrobenzoic acid, 20 weight per cent meta-nitrobenzoic acid and one weight per cent ortho-nitrobenzoic acid. In Runs Nos. II and III, the para-nitrobenzoic acid content was 86 and 77.7 weight per cent respectively, meta-used as bacteriostatic agents as anti-viral agents and as plant growth inhibitors. Para-nitrobenzoic acid is particularly attractive, since it can be hydrogenated, using conventional means, to obtain para-aminobenzoic acid. The latter can be homopolymerized to give polyamides having high tensil strength and high temperature stability (Encyclopaedia of Polymer Science and Technology, Volume 10, pages 347 to 460, 1972, Interscience Publishers, N.Y.) or can be copolymerized with diphenylamines or terephthalic acids to obtain linear polymers suitable for use as fibers (U.S. Pat. Nos. 3,817,941 and 3,819,587).

Obviously, many modifications and variations of the invention, as hereinabove set forth, can be made without departing from the spirit and scope thereof, and therefore only such limitations should be imposed as are indicated in the appended claims.

We claim:

1. A process for converting stilbene or bibenzyl to a product predominating in para-nitrobenzoic acid which comprises nitrating said compound with nitric acid and then oxidizing the nitrated product with nitric acid, said nitration being conducted with an aqueous nitric acid solution having a concentration of about 40 to about 95 weight per cent at a temperature of about −20° to about 100° C. over a period of about 15 minutes to about 12 hours and said oxidation being conducted with an aqueous nitric acid solution having a concentration of about 5 to about 50 weight per cent at a temperature of about 160° to about 220°C. for about one-half to about 12 hours.

2. The process of claim 1 wherein said aromatic compound is trans-stilbene.

3. The process of claim 1 wherein said aromatic compound is bibenzyl.

4. The process of claim 1 wherein the nitric acid concentration during nitration is in the range of about 70 to about 90 per cent.

5. The process of claim 1 wherein the temperature during nitration is in the range of about −10° to about 60° C.

6. The process of claim 1 wherein the nitric acid concentration during oxidation is in the range of about 10 to about 40 per cent.

7. The process of claim 1 wherein the temperature during oxidation is in the range of about 170° to about 190°C.

* * * * *